US00PP27448P2

(12) United States Plant Patent
Giesen

(10) Patent No.: US PP27,448 P2
(45) Date of Patent: Dec. 6, 2016

(54) ***LOBELIA* PLANT NAMED 'LOBZ0009'**

(50) Latin Name: ***Lobelia erinus* L.**
Varietal Denomination: LOBZ0009

(71) Applicant: SYNGENTA PARTICIPATIONS AG, Basel (CH)

(72) Inventor: Eric Giesen, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/756,091

(22) Filed: Jul. 30, 2015

(51) Int. Cl.
*A01H 5/02* (2006.01)

(52) U.S. Cl.
USPC ..... Plt./451

(58) Field of Classification Search
USPC ..... Plt./451
See application file for complete search history.

*Primary Examiner* — Susan McCormick Ewoldt
(74) *Attorney, Agent, or Firm* — Joshua L. Price

(57) ABSTRACT

A new *Lobelia* plant named 'LOBZ0009' particularly distinguished by large, purple flowers, strong stems with long inflorescences, dark green foliage, medium sized leaves, medium sized plant size, free branching, Mounding to trailing plant habit.

1 Drawing Sheet

Latin name of the genus and species of the plant claimed: *Lobelia erinus* L.

Varietal denomination: 'LOBZ0009'.

BACKGROUND OF THE NEW PLANT

The present invention comprises a new and distinct cultivar of *Lobelia*, botanically known as *Lobelia erinus*, and hereinafter referred to by the cultivar name 'LOBZ0009'.

'LOBZ0009' is a product of a planned breeding program. The new cultivar has large, purple flowers, strong stems with long inflorescences, dark green foliage, narrow leaves, free branching, and a medium sized, large and open trialing plant habit.

'LOBZ0009' originated from a hybridization made in May 2009 in Andijk, The Netherlands.

The female parent was an unpatented, proprietary *Lobelia* plant designated 'LOB08-315-1', having larger flowers, darker green leaves and a mounding trailing plant habit, while plant habit of 'LOBZ0009' is distinctly more trailing.

The male parent of 'LOBZ0009' was the proprietary *Lobelia* plant designated 'LOB7-185-1' (unpatented), having purple flowers, more light green and glossy foliage, and longer stems than 'LOBZ0009'.

The resulting seeds were sown in June 2009 and 'LOBZ0009' was selected as one flowering plant within the progeny of the stated cross in September 2009 in a controlled environment in Andijk, The Netherlands.

The first act of asexual reproduction of 'LOBZ0009' was accomplished when vegetative cuttings were propagated from the initial selection in the summer of 2010 in a controlled environment in Andijk, The Netherlands.

BRIEF SUMMARY OF THE INVENTION

Horticultural examination of plants grown from cuttings of the plant initiated in the spring of 2014 in Andijk, The Netherlands, and continuing thereafter, has demonstrated that the combination of characteristics as herein disclosed for 'LOBZ0009' are firmly fixed and are retained through successive generations of asexual reproduction.

'LOBZ0009' has not been observed under all possible environmental conditions. The phenotype may vary significantly with variations in environment such as temperature, light intensity, and day length.

A Plant Breeder's Right for this cultivar was applied for with the European Union on Jun. 26, 2014, No. 2014/1695. 'LOBZ0009' has not been made publicly available prior to the filing of this application.

The following traits have been repeatedly observed and are determined to be basic characteristics of the new variety. The combination of these characteristics distinguishes this *Lobelia* as a new and distinct variety.

DESCRIPTION OF THE PHOTOGRAPHS

The accompanying photograph drawings show typical flower and foliage characteristics of 'LOBZ0009' with colors being as true as possible with an illustration of this type.

Figure 1:
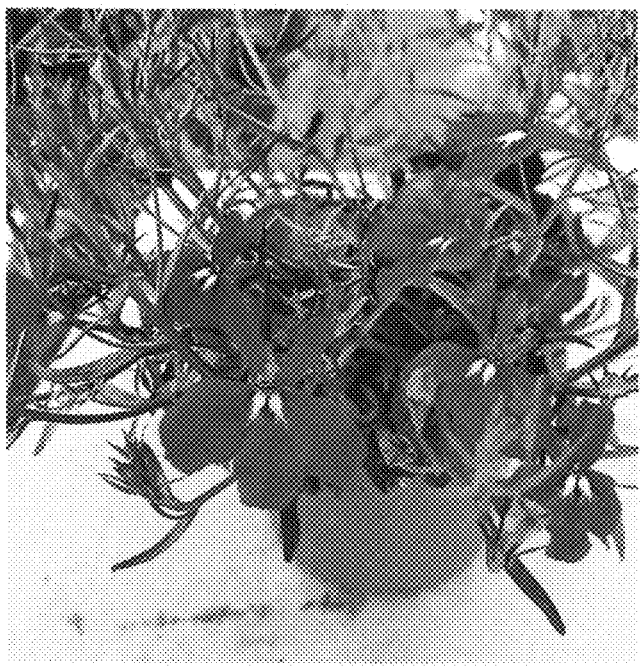
Figure 2:
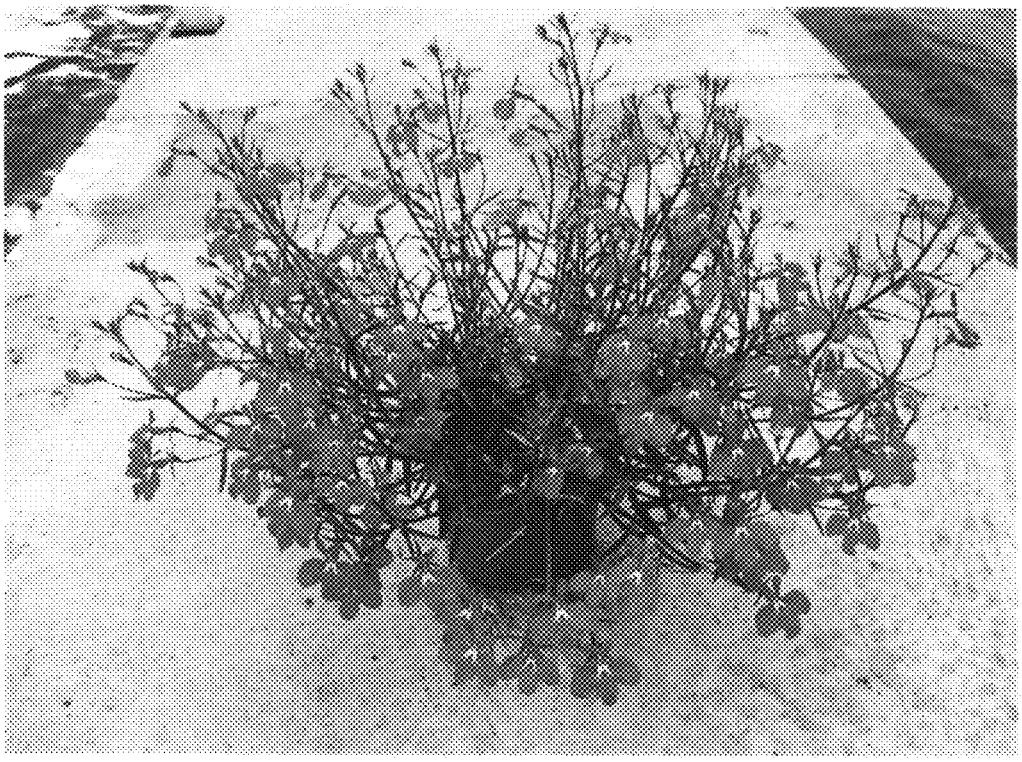

The photographic drawings show in FIG. 1 a close-up of the flowers and in FIG. 2 a flowering potted plant of the new variety.

DETAILED BOTANICAL DESCRIPTION

The aforementioned photographs were taken in Apr. 28, 2015 from plants grown in a greenhouse trial in Andijk, The Netherlands. These plants were grown in 10.5 cm pots and were approximately 11 weeks of age. The close-up photograph was taken at the same time.

The observations and measurements were taken in Andijk, The Netherlands on Jun. 25, 2015 on 11 week old plants that were growing indoors in 10.5 cm containers. Culture of these plants had started in April 2015 with the planting of rooted cuttings, one plant per container, and pinching about two weeks later.

Color references are made to The Royal Horticultural Society Colour Chart (R.H.S.) 2001.

TABLE 1

DIFFERENCES BETWEEN THE NEW VAREITY 'LOBZ0009' and A MOST SIMILAR VARIETY

| | 'LOBZ0009' | 'TECH HEVIO', commercially known as 'Techno violet' |
|---|---|---|
| Leaves: | Smooth, darker color | Hairy, lighter color |
| Leaf size: | Large, broader | Small(er) |
| Flower, diameter: | Larger: 2.1 cm | Smaller: 1.4 cm |
| Flower color: | N81A, mature flowers keep the same color | N81C to 76B, older flowers get lighter color |

Plant:

*Growth and habit*.—Vigorous growth habit; dense, and freely branching with medium internodes, trailing.

*Height*.—About 15-20 cm (from top of soil).

*Height* (*inflorescence included*).—About 24-32 cm.

*Width* (*horizontal diameter*).—From 30-45 cm.

*Branching characteristics*.—10 main stems, each with 3-4 secondary branches.

*Time to produce a finished flowering plant*.—About 12 weeks for a 12 cm pot.

*Garden performance*.—Used as patio planters, in mixed container plantings, or in garden beds.

*Time to initiate and develop roots*.—21-28 days at 20-23° centigrade.

Roots:

*Number of days to initiate roots*.—About 15 days at about 22 degrees C.

*Number of days to produce a rooted cutting*.—21-25 days.

*Type*.—Fibrous and freely branching.

*Color*.—RHS N155B.

Foliage:

*Arrangement*.—Alternate.

*Leaf shape*.—Lanceolate.

*Apex*.—Mucronulate.

*Base*.—Attenuate.

*Margin*.—Entire to slightly incised.

*Leaf length*.—2.8-4.5 cm.

*Leaf width*.—0.8-1.1 cm.

*Immature leaf, color upper surface*.—RHS 136B.

*Immature leaf, color lower surface*.—RHS 137B.

*Mature color upper surface*.—RHS 145A.

*Mature color lower surface*.—RHS 146A.

*Venation type*.—Pinnate.

*Venation color, upper surface*.—Indistinct.

*Venation color, lower surface*.—Indistinct.

*Texture*.—Smooth.

*Petiole*.—No petiole, leaves are sessile.

Stem:

*Characteristics*.—With slightly strengthened, protruding edges, side branches are developed at almost every node.

*Stem length*.—18-25 cm.

*Diameter*.—0.3-0.4 cm.

*Internode length*.—2.0-3.5 cm.

*Color*.—Mainly RHS 137A.

*Texture*.—Very sparsely hirsute.

Inflorescence:

*Type*.—Raceme, composed of single flowers in an alternate arrangement with one flower per node, subtended by a small leaflet.

*Blooming habit*.—Continuously through the growing season from spring to the fall.

*Quantity of inflorescences per plant*.—About 25 per container/14 per plant.

*Quantity of flowers per inflorescence*.—Up to 15 open flowers, and additional buds.

*Lastingness of individual blooms on the plant*.—5-7 days, depending on temperature.

*Fragrance*.—None.

*Inflorescence length*.—1.9-2.2 cm.

Peduncle:

*Color*.—From RHS 144B to RHS 145A.

*Length*.—8-12 cm.

*Diameter*.—0.3 cm.

*Texture*.—Pubescent.

Pedicels:

*Color*.—RHS 138A.

*Length*.—2.3-3.2 cm.

*Diameter*.—0.1 cm.

*Texture*.—Glabrous.

Flower:

*Corolla type and shape*.—Single, zygomorphic; upper lip is formed by two small petals, lower lip has three larger petals; petals are fused at the base forming a relatively long funnel-shaped tube.

Flower bud:

*Shape*.—Oblong.

*Length*.—1.8-2.0 cm.

*Diameter*.—0.3-0.4 cm.

*Color* (*at tight bud*).—RHS 81D.

Immature flower:

*Main color upper surface*.—RHS 81B.

*Main color lower surface*.—RHS 81A.

*Immature flower, width*.—1.1 cm.

Mature flower:

*Flower*, (*horizontal*) *length*.—2.1 cm.

*Flower*, (*horizontal*) *width*.—2.1 cm.

*Flower, vertical length* (*depth*).—2.2 cm.

*Color upper lip, upper surface*.—RHS 81A.

*Color upper lip, lower surface*.—RHS 81A.

*Upper petal lobes, length* (*from the tube opening*).—1.1-1.2 cm.

*Upper petal lobes, width*.—0.3-0.4 cm.

*Color lower lip, upper surface*.—RHS 82B.

*Color lower lip, lower surface*.—RHS 82C.

*Nectaries at base of lower petals*.—RHS 145C.

*Lower petal lobes, length* (*from the corolla opening*).—1.2-1.5 cm.

*Lower petal lobes, width*.—0.8-1.0 cm.

*Tube, color* (*outside*).—RHS 80C.

*Tube length*.—0.9-1.0 cm.

*Tube width*.—0.3-0.4 cm.

Petal (lobes):

*Shape*.—Obovate.

*Apex shape*.—Acute.

*Base*.—Fused.

*Margin*.—Entire.

*Texture upper surface*.—Glabrous.

*Texture lower surface*.—Smooth.

Calyx:

*Shape*.—5 sepals in a whorl, slanting outwards, fused at base.

*Sepal color*.—RHS 138A.

*Sepal length* (*free ends*).—0.8 cm, respective 1.1 cm when including the funnel shaped part.

*Width*.—0.3 cm.
*Shape*.—Ligulate.
*Apex*.—Acute.
*Base*.—Fused.
*Texture*.—Smooth.

Reproductive organs:

*Stamens*.—Quantity: 5. Filament, color: RHS 155B. Filament length: 0.5-0.7 cm. Filament, diameter: 0.1 cm. Anther color: RHS 187B. Anther length: 0.2 cm. Pollen amount: Little. Pollen color: RHS 13B to RHS 13C.

*Pistil*.—Quantity per flower: 1. Length: 1.0 cm. Stigma color: RHS 147B. Stigma length: 0.2 cm. Style color: RHS 145B. Style length : From 0.7-0.8 cm.

Fruit and seed set: Occasionally observed outdoors.

Disease and insect resistance: Resistance and susceptibility typical for the species, no special observations made.

The invention claimed is:

1. A new and distinct cultivar of *Lobelia* plant named 'LOBZ0009' as shown and described herein.

* * * * *